United States Patent [19]

Brandes et al.

[11] Patent Number: 4,803,227

[45] Date of Patent: Feb. 7, 1989

[54] AMINOALKYL ETHERS OF PHENOLS AS ANTICANCER AGENTS FOR THE BREAST AND COLON

[75] Inventors: Lorne J. Brandes, Winnipeg; Mark W. Hermonat, Mississauga, both of Canada

[73] Assignee: The University of Manitoba, Winnipeg, Canada

[21] Appl. No.: 70,207

[22] Filed: Jul. 6, 1987

Related U.S. Application Data

[63] Continuation-in-part of Ser. No. 699,265, Feb. 7, 1985, abandoned.

[30] Foreign Application Priority Data

Feb. 14, 1984 [CA] Canada ................................. 447369

[51] Int. Cl.[4] .................. A61K 31/135; A61K 31/535
[52] U.S. Cl. .................................... 514/651; 514/239.2
[58] Field of Search ................................ 514/240, 651

[56] References Cited

PUBLICATIONS

Cheney et al., J. of Am. Chem. Society, 71 (1949), pp. 60–64.

Primary Examiner—Jerome D. Goldberg
Attorney, Agent, or Firm—Alan A. Thomson

[57] ABSTRACT

The use of (a) N,N-dialkyl-2-[(4-phenylmethyl)phenoxy]ethanamine and N-morpholino-2-[(4-phenylmethyl)-phenoxy]ethanamine compounds and their salts, as anticancer agents, is described. These compounds bind significantly to the anti-estrogen binding sites but only poorly to the estrogen receptor sites, and are cytotoxic to cancer cells. Compositions including mixtures of these ethanamine compounds (a) with (b) therapeutically active anticancer compounds such as tamoxifen, have been found particularly beneficial.

5 Claims, 3 Drawing Sheets

AMINOALKYL ETHERS OF PHENOLS AS ANTICANCER AGENTS FOR THE BREAST AND COLON

This is a continuation-in-part application of patent application Ser. No. 06/699,265 filed Feb. 7, 1985 (now abandoned).

BACKGROUND OF THE INVENTION

Anti-estrogen compounds are now widely used in the treatment of human breast cancer. One of the most widely used of these compounds is 1-(p-β-dimethylaminoethoxyphenyl)-trans-1,2-diphenylbut-1-ene (tamoxifen). A description of a pharmaceutical composition containing 1-(p-β-dimethylaminoethoxyphenyl)-trans-1-(p-hydroxyphenyl)-2-phenylbut-1-ene is given in D. N. Richardson's U.S. Pat. No. 4,198,435. The exact mechanism of action of these compounds is not known and while it is well documented that tamoxifen and related triphenylethylene compounds compete for the estrogen receptor (ER), the actual mechanism(s) by which they inhibit tumor cell growth and/or cause cell death has been obscure. More recently, a second high-affinity saturable binding site (anti-estrogen binding site, AEBS), which may interact with the alkylaminoethoxy side chain of triphenylethylene derivatives has been described in a range of normal human tissues and in human breast cancer cells.

N,N-dimethyl-2[(2-phenylmethyl)phenoxy]ethanamine (also known as phenyltoloxamine) and its water soluble hydrochloride are described by L. C. Cheney et al, J. Am. Chem. Soc., 71, 60–63, 1949. A slightly different synthesis of the diethyl form of the same ortho compound is given in H. J. Engelbrescht's West Germany Pat. No. 1,269,134 and his U.K. Pat. No. 961,275. These compounds have pronounced anti-histamine effects.

SUMMARY OF THE INVENTION

One aspect of this invention is concerned with anti-cancer compositions comprising (a) a compound of the formula

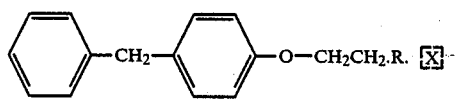 (1)

wherein R is selected from
(i)

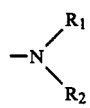

wherein $R_1$ and $R_2$ are alkyl groups containing 1 to 2 carbon atoms, and,
(ii)

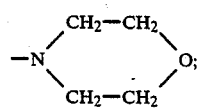

and X when present, is a physiologically-acceptable salt forming acid; and (b) at least one therapeutically active anticancer compound.

Particular compounds (a) of interest are those wherein $R_1$ and $R_2$ are ethyl groups, or R is a morpholino group.

This invention includes compositions wherein the compound (a) has X present preferably as hydrochloric acid.

Such compositions include those wherein the therapeutically active anticancer compound (b) is 1-(p-β-dimethylaminoethoxyphenyl)-trans-1,2-diphenyl-but-1-ene-, also known as tamoxifen, or a pharmaceutically acceptable salt thereof.

The morpholino compounds (a) closely resemble the dialkyl compounds (a) with the addition of an oxygen bridge between the two —$CH_2$—$CH_2$— groups, and the activity is similar.

According to this invention a method of treatment of cancer comprises administering, by at least one of oral and parenteral routes, at least one of the above compounds (a) of formula (1) within the unit dose range effective to inhibit cancer cell growth and at least about 8 mg/kg body weight. Such compounds may be admixed with at least one therapeutically active anticancer compound (b) and administered in a similar way within a similar dose range.

DETAILED DESCRIPTION OF THE INVENTION

Figure 1A:
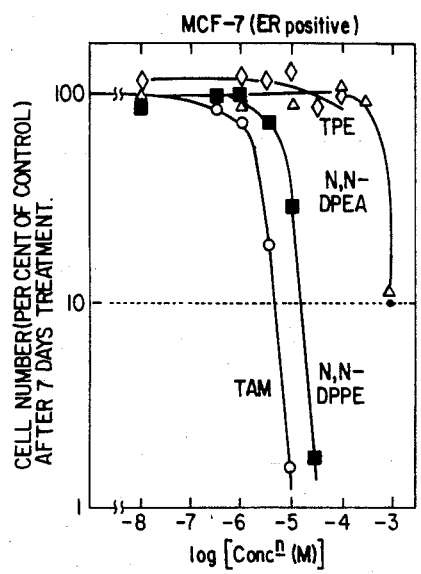
FIG. 1A shows the survival of ER- and AEBS-positive MCF-7 human breast cancer cells after 7 days of exposure to various concentrations of tamoxifen (open circles), N,N-diethyl-2-[(4-phenylmethyl)phenoxy]ethanamine hydrochloride (N,N-DPPE) (closed squares), N,N-diethyl-2-phenoxyethylamine hydrochloride (N,N-DPEA) (open triangles) and triphenylethylene (open diamonds). Concentrations are shown on the x-axis.

The method of manufacturing these compounds of the formula:

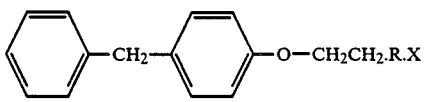

(2)

(wherein R and X are as defined in the Summary of the Invention) which we have found most suitable comprises:

(a) mixing para-benzyl phenol with an aqueous solution of the hydroxide of an alkali metal, for example, sodium hydroxide, (b) adding to the mixture of step (a), an aqueous solution of a compound of the formula:

(3a)

wherein R and X are as defined above and Y is a halide selected from the group consisting of chloride and bromide. Two compounds (3a) that we found suitable were β-diethylaminoethylchloride hydrochloride and β-morpholinoethylchloride hydrochloride. An essentially non-aqueous layer results, (c) heating the mixture resulting from step (b) to clear the essentially non-aqueous layer (e.g. to between 55° C. and 60° C. for 30 to 60 minutes), (d) separating the essentially non-aqueous layer of step (c) and washing said layer with, for example, aqueous sodium hydroxide, to remove impurities, (e) reacting the non-aqueous layer of step (d) with an aqueous solution of a physiologically acceptable salt forming acid, such as hydrochloric acid to yield an essentially non-aqueous layer and an essentially aqueous layer, (f) evaporating the aqueous layer of step (e) to dryness, and (g) following step (f) by (i) dissolving the product of step (f) in warmed isopropanol, (ii) recrystallizing the product of step (i) by, for example, cooling on ice and, (iii) washing the crystals resulting from step (ii) with a suitable non-polar solvent, such as ether, said crystals being compound (2).

A compound which is cytotoxic to breast cancer cells similarly to tamoxifen, is N,N-diethyl-2-[(4-phenylmethyl)phenoxy]ethanamine hydrochloride of the formula:

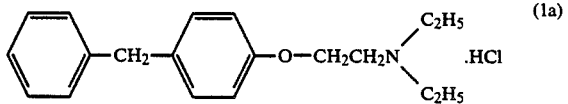

(1a)

A method of manufacturing this latter compound which we have found most suitable comprises:

(a) mixing para-benzyl phenol with an aqueous solution of sodium hydroxide, (b) adding to the mixture of step (a) an aqueous solution of β-diethylaminoethylchloride hydrochloride of the formula:

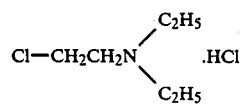

wherein an essentially non-aqueous layer results;

(c) heating to clear the essentially non-aqueous layer formed as a result of step (b), (d) separating the uppermost essentially non-aqueous layer of step (c) and washing said layer with an aqueous solution of the hydroxide of an alkali metal, (e) reacting the non-aqueous layer of step (d) with an aqueous solution of hydrochloric acid to yield an essentially non-aqueous layer and an essentially aqueous layer;

(f) evaporating the aqueous layer of step (e) to dryness and recovering the residue (1a).

N-morpholino-2-[(4-phenylmethyl)phenoxy]ethanamine hydrochloride of the formula:

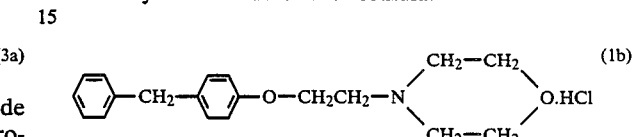

(1b)

may be made in a similar way by substituting, in step (b), β-morpholinoethylchloride hydrochloride for β-diethylaminoethylchloride hydrochloride.

The preferred synthesis of N,N-diethyl-2-[(4-phenylethyl)phenoxy]ethanamine hydrochloride (1a) comprises, by way of example, (a) mixing about 9 parts by weight of para-benzyl phenol with about 4 parts of sodium hydrochloride in about 25 parts of water, (b) adding to the mixture of step (a), dropwise over the period of about an hour, a solution of about 10 parts β-diethylaminoethylchloride hydrochloride in 5 parts of water, (c) heating the mixture of step (b) to about 55° C. to 60° C. for about 30 min. to 60 min. to clear an essentially non-aqueous layer;

(d) separating the essentially non-aqueous layer of step (c) and washing it, for example, with about three times with an aqueous solution of sodium hydroxide of about 5% strength and once with distilled water;

(e) reacting the non-aqueous layer of step (d) with about an equal volume of about 10% hydrochloric acid solution to yield an essentially non-aqueous layer and an essentially aqueous layer;

(f) evaporating the aqueous layer resulting from step (e) to dryness; and (g) purifying the residue of step (f) by dissolving in a minimal volume of isopropanol at about 45° C. to 50° C. and recrystallizing, for example, on ice at least once and subsequently washing the resulting crystals at least once with a suitable non-polar solvent, such as ether, to yield (1a).

Preferably, N-morpholino-2-[(4-phenylmethyl)-phenoxy]ethanamine hydrochloride (MPPE) (1b) may be made in a similar way by substituting, in step (b), a solution of about 10 parts β-morpholinoethylchloride hydrochloride in 5 parts of water for the 10 parts of β-diethylaminoethylchloride hydrochloride in 5 parts of water.

Proportions of compounds given reflect approximate proportions used. Specific gram proportions given are not meant to be limiting and can be varied around idealized stoichiometric proportions in the usual way known to those skilled in the art.

Method of manufacture of N,N-diethyl-2[(4-phenylmethyl)phenoxy]ethanamine hydrochloride (1a)

4.35 g of NaOH were dissolved in 25 ml of distilled water and to this solution was added 9.2 g of para-benzylphenol while stirring at room temperature (18°–22° C.). To this was added, dropwise over the period of an hour, a solution of 10.2 g β-diethylaminoethylchloride hydrochloride in 5 ml of distilled water. The reaction mixture was then stirred for 30 min and heated to about 60° C. for 30–60 min to yield an essentially non-aqueous layer. At this stage, three layers were distinguishable: a cloudy beige bottom layer comprising approximately 60% of the total volume, a dark brown middle layer comprising approximately 30%, of the total volume, and an orange, oily, viscous layer comprising approximately 10% of the total volume. The layers were separated and tested for their polarity by the water drop test. The non-aqueous layer was washed three times with equal volumes of 5% NaOH, once with an equal volume of distilled water and 50 ml of ether added (the addition of ether appears to improve yield). The resulting mixture was treated with an equal volume of 10% HCl to yield the hydrochloride salt. The aqueous layer resulting from this treatment was retained and divided among petri plates to facilitate evaporation overnight. The resulting orange-white residue was dissolved in a minimal volume of warmed (45°–50° C.) isopropanol and then recrystallized on ice. This solution-crystallization sequence was repeated once again before the now white crystals were washed with approximately 5 ml ether while on filter paper under vacuum. The crystals (1a) were allowed to dry in a dessicator under vacuum for 3 days.

The molecular weight of the hydrochloride (1a) was confirmed to be 319.88. Mass spectrometry studies showed the non-hydrochloride to have a molecular weight of 283.4.

Evidence in support of the proposed structure comes from Nuclear Magnetic Resonance (NMR) and Mass Spectroscopy (MS) studies. MS studies showed N,N-DPPE without the hydrogen chloride grouping to have a molecular weight of 283.4. N-morpholino-2-[(4-phenylmethyl)phenoxy]ethanamine hydrochloride (MPPE) (1b) was made in a similar way by substituting, in step (b), a solution of about 10.2 parts β-morpholinoethylchloride hydrochloride in 5 parts of water for the 10.2 parts of β-diethylaminoethylchloride hydrochloride in 5 parts of water.

N-morpholino and N,N-diethyl-2-[(4-phenylmethyl)-phenoxy]ethanamine HCl are closely related 2-ringed diphenylmethane derivatives which bind significantly to AEBS but only weakly to ER while effecting cytotoxicity on MCF-7 human breast cancer cells. The cytotoxic effects of these and other compounds correlate positively with the ability to compete with [$^3$H]-tamoxifen for binding to AEBS but not with [$^3$H]-17 β-estradiol for binding to ER.

These N-morpholino and N,N-dialkyl-2-[(4-phenylmethyl)phenoxy]ethanamines and their salts may be used with or without inert carriers and may be administered in a dose, of the active compound(s), effective to inhibit cancer cell growth and usually at least about 8 and preferably within the range of about 8 to 40 mg/kg body weight. Means of administration include, but are not limited to, oral or parenteral pathways.

These compounds (a) are most advantageously used in admixture with at least one other therapeutically active anticancer compound (b) particularly for example, another di-or-tri-phenyl-containing antiestrogen compound such as tamoxifen. Most suitably the proportion of (a) is from about 1 to about 10 times the amount of tamoxifen e.g. see FIG. 1D.

The examples given below are illustrative.

EXAMPLE 1

The following compounds have been evaluated for their ability to compete with [$^3$H]-tamoxifen base (70 ci/mmol); New England Nuclear) for AEBS using a microplate adaptation of the standard dextran-coated charcoal assay as described in L. J. Brandes and M. W. Hermonat, Cancer Res., 43, 2831–2835, 1983,: tamoxifen citrate (TAM; Sigma Chemical Co.), triphenylethylene (TPE: Aldrich Chemical Co.), N,N-diethyl-2-phenoxyethylamine HCl (N,N-DPEA), N,N-diethyl-2-[4(phenylmethyl)phenoxy]ethanamine HCl (N,N-DPPE) and its N,N-dimethyl ortho-isomer, the antihistamine phenyltoloxamine (K and K Chem. Co.). The single ring structure, N,N-DPEA, was synthesized from phenol (Aldrich) and 2-diethylaminoethyl chloride HCl (Aldrich) using the method of S. M. Poling et al, Phytochemistry 14, 1933–1938, 1975.

Figure 1B:
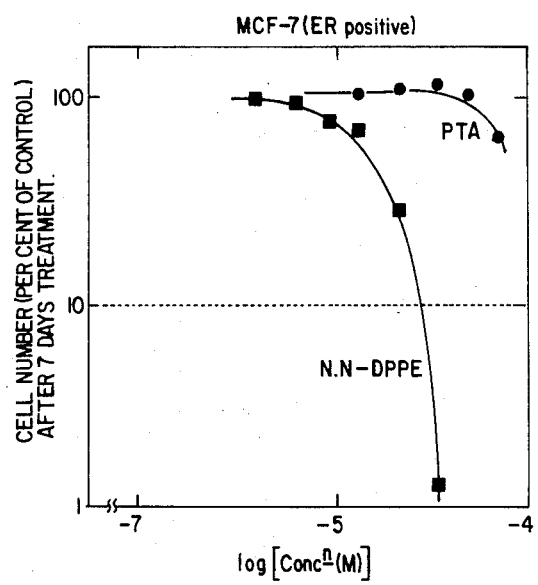
FIG. 1B shows the survival of MCF-7 cells after 7 days of exposure to various concentrations of two diphenylmethane derivatives: N,N-DPPE (para-isomer) (closed squares) and phenyltoloxamine (PTA) (ortho-isomer) (closed circles).
Figure 1C:
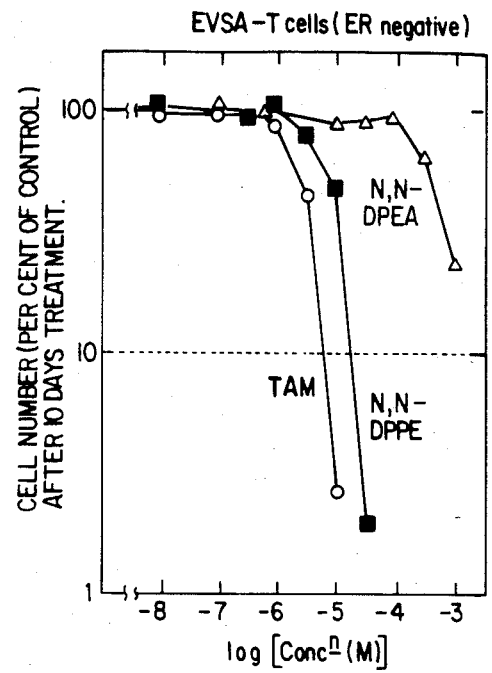
FIG. 1C shows the survival of ER-negative, AEBS-positive EVSA-T human breast cancer cells after 10 days of exposure to various concentrations of tamoxifen (open circles), N,N-DPPE (closed squares) and N,N-DPEA (open triangles). A longer exposure time (10 days) was employed because this cell line is slower growing than the MCF-7 cell line.

FIGS. 1a and 1c demonstrate the ability of the test compounds to effect cytotoxicity on ER-positive, AEBS-positive MCF-7 human breast cancer cells and on ER-negative, AEBS-positive EVSA-T cells. In the case of MCF-7 cells, approximately $2 \times 10^4$ MCF-7 cells were seeded into duplicate 25 cm tissue culture flasks containing Dulbecco's modified Eagle's medium supplemented with insulin (10 μg/ml), glucose (3.5 μg/ml) and 5% dextran coated charcoal-stripped fetal calf serum to which was added increasing concentrations of the compound to be tested. Cells were allowed to grow for 7 days with one change of medium containing the test compound on day 4. On day 7 the cells were removed from the flasks by treatment with $1 \times 10^{-3}$M ethylenediaminetetraacetic acid (EDTA). Total cell number at each concentration was determined by Coulter counter. The average % error for the growth inhibition was 11%. D (that concentration required to elicit a 90% reduction in cell number relative to the control after 7 days of treatment) was determined for each compound. Both MCF-7 cells and EVSA-T cell lines are rich in AEBS; the concentration in MCF-7 microsomes is $1120 \pm 299$ femtomoles mg$^{-1}$ protein and in EVSA-T microsomes is $648 \pm 166$ femtomoles mg$^{-1}$ protein.

The concentration of each compound at which 90% cell reduction relative to the control occurs ($D_{10}$), correlates positively with its relative specific binding affinity for AEBS and is shown in Table 1. In this regard, triphenylethylene (TPE), which at higher concentrations competes with [$^3$H] 17 β-estradiol for ER, but which at all concentrations tested fails to compete with [$^3$H]-tamoxifen for AEBS demonstrates no cytotoxic effect on MCF-7 cells after 7 days of exposure (FIG. 1a and Table 1).

TABLE 1

The relationship between cytotoxicity and relative specific binding affinity to AEBS in 2 microsomal preparations for various compounds RSBA* (M) for AEBS

| Compound | MCF-7 microsomes | Rat liver microsomes | $D_{10}^+$ (M) |
| --- | --- | --- | --- |
| Tamoxifen | $1 \times 10^{-10}$ | $2 \times 10^{-9}$ | $4.8 \times 10^{-6}$ |

TABLE 1-continued

The relationship between cytotoxicity and relative specific binding affinity to AEBS in 2 microsomal preparations for various compounds
RSBA* (M) for AEBS

| Compound | MCF-7 microsomes | Rat liver microsomes | $D_{10}^+$ (M) |
|---|---|---|---|
| N,N—DPPE (1a) | $7 \times 10^{-7}$ | $4 \times 10^{-8}$ | $1.6 \times 10^{-5}$ |
| MPPE (1b) | $6.6 \times 10^{-7}$ | N.D.++ | $1.6 \times 10^{-5}$ |
| Phenyltoloxamine | N.D.++ | $2 \times 10^{-6}$ | $4.8 \times 10^{-5}$ |
| N,N—DPEA | $8 \times 10^{-5}$ | $4 \times 10^{-5}$ | $1.1 \times 10^{-3}$ |
| Triphenylethylene | No affinity | N.D. | No effect |

*Relative specific binding affinity (RSBA) is the concentration of cold competitor required to displace 50% of the specifically bound label and expresses the affinity of the test compound for the receptor relative to that of the labelled specific ligand, in this instance $1.5 \times 10^{-9}$ M [$^3$H]—tamoxifen
+$D_{10}$ is the concentration of the test substance required to effect a 90% reduction in the number of MCF-7 cells after 7 days of exposure
++not determined MPPE produced a curve almost identical to that produced by N,N-DPPE when the compounds, along with tamoxifen, were tested for cytotoxicity on MCF-7 human breast cancer cells in experiments similar to those illustrated in FIG. 1a.

The position at which the 2 rings are bound by the methyl bridge in forming the diphenylmethane derivatives has a marked effect on affinity for AEBS and an even greater effect on cytotoxicity for MCF-7 cells as shown in FIG. 1b, where N,N-DPPE demonstrates significantly greater cytotoxicity after 7 days of treatment than its dimethyl orthoisomer, phenyltoloxamine; the latter compound becomes significantly cytotoxic only at concentrations $>1\times10^{-4}$M (data not shown).

Figure 1D:
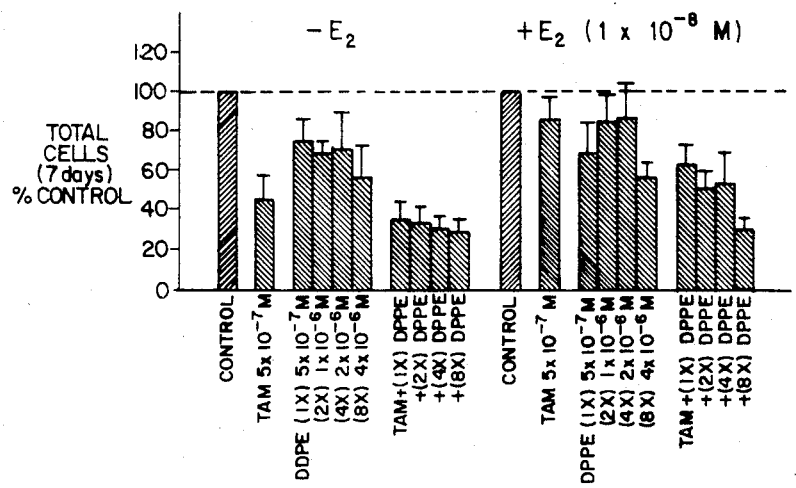
FIG. 1D shows the growth inhibition of MCF-7 cells after 7 days of exposure to tamoxifen (TAM) alone ($5 \times 10^{-7}$M), increasing ratios of N,N,-DPPE alone (1x,2x,4x,8x, TAM concentration) and TAM plus N,N,-DPPE, all in the presence and absence of estradiol ($E_2$).

FIG. 1D demonstrates the ability of N,N-DPPE to influence the effect of tamoxifen on growth of MCF-7 cells at a concentration of tamoxifen normally reversible by estradiol. Significant inhibition after 7 days of exposure to tamoxifen alone is seen; this effect is largely but not completely reversed by the addition of $1\times10^{-8}$M estradiol. The MCF-7 cells treated with increasing concentrations of N,N-DPPE alone in the absence of estradiol also showed significant growth inhibition, but in all cases, less than that for tamoxifen; however, in the presence of estradiol, N,N-DPPE demonstrated significantly ($P<0.001$) more inhibition than tamoxifen because, as opposed to tamoxifen, there is no significant reversal of its effect by estradiol. The combination of N,N-DPPE plus tamoxifen demonstrated significantly ($p<0.05$) more inhibition than tamoxifen alone in the absence of estradiol; this effect was even more significant ($p<0.001$) in the presence of estradiol.

Figure 2:
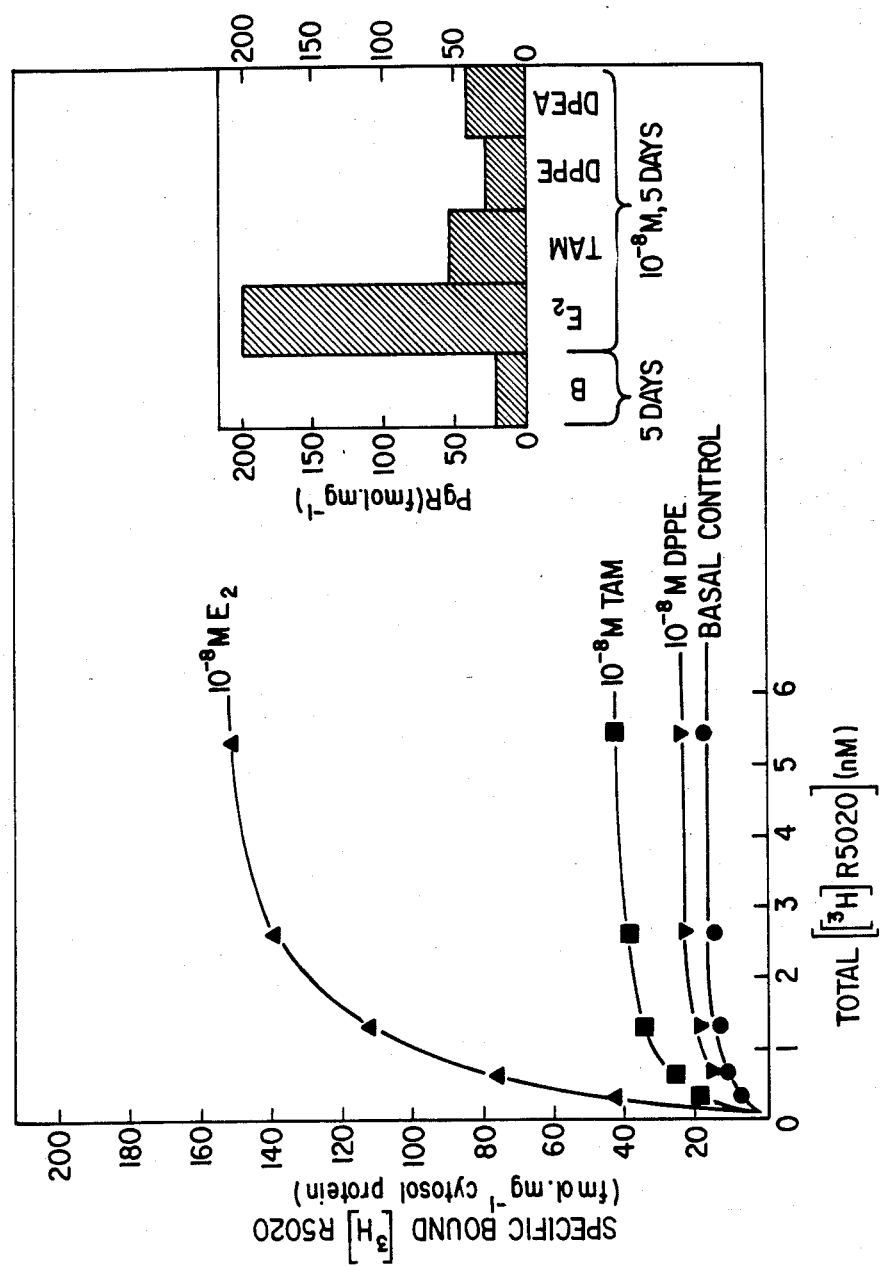
FIG. 2 shows the effect of 5 days of pre-incubation with $1 \times 10^{-8}$M 17 β-estradiol (E2, closed triangles), $1 \times 10^{-8}$M tamoxifen (closed squares) and $1 \times 10^{-8}$M, N,N-DPPE (closed inverted circles) on progesterone receptor (PgR) concentration in MCF-7 cells. The basal (control) PgR levels are shown as closed circles.

FIG. 2 demonstrates the inability of N,N-DPPE to functionally interact with ER as signified by its failure to induce significant synthesis of progesterone receptor (PgR) above control levels; conversely, 17 β-estradiol increased PgR by almost 10-fold while at this low concentration tamoxifen (as previously shown by W. L. McGuire et al, Molecular Pharmacology and Antitumor Activity, p. 339-354, ed. R. L. Sutherland and V. C. Jordan, Academic Press, New York, 1981) had a lesser effect, increasing PgR by 2.5-fold. Measurement of PgR was carried out by incubating cytosols for 4 h at 4° C. in the presence of the labelled synthetic progesterone R5020 in concentrations ranging between 0.2 and $5\times10^{-9}$M with and without a 100-fold excess of unlabelled R5020 to estimate non-specific binding. Cytosols were diluted 1.25-fold and all PgR values except the final value at saturation are expressed as such. Concentration of PgR was calculated by Scatchard analysis and expressed as the number of femtomoles/mg crude cytosol protein. To obtain basal (control) PgR levels, cells are incubated in Dulbecco's modified Eagle's medium containing 10% dextran-coated charcoal-stripped fetal calf serum for 5 days.

The results suggest a biological role for the antiestrogen binding site as a mediator of growth. Compounds such as N,N-DPPE may therefore be antiproliferative and cytotoxic by binding to the anti-estrogen binding site. The findings for Tamoxifen suggest that in addition to ER, AEBS antagonism may be a second important mechanism of action by which this compound effects cytotoxicity, and may explain the demonstration by others that resistance to Tamoxifen in a population of MCF-7 breast cancer cells was associated with a loss in demonstratable AEBS.

It is expected that the addition of DPPE to Tamoxifen will allow for a greater antagonism of AEBS with resulting greater antiproliferative and cytotoxic effects than Tamoxifen alone. Such a combination would retain the possible benefits of the ER antagonism demonstrated by Tamoxifen while increasing the antagonism of AEBS by the mixture of both compounds together.

While the use of a combination of N,N-DPPE and Tamoxifen is expected to be more effective in the treatment of hormonally-responsive breast cancers, the use of N,N-DPPE alone may be effective in other forms of cancer, such as colon cancer, which does not contain ER.

EXAMPLE 2

Tests were carried out in cancerous female rats to investigate the effect of N,N-DPPE on colon tumors. The rats had been subcutaneously implanted with colon carcinoma (3C872) and were cancerous. The N,N-DPPE was given intramuscularly (as a 0.9% saline solution) twice daily for 7 days at 3 dose levels per injection from 8 to 32 mg/kg, to 10 rats at each dose level. The wt. of the tumor was measured after the 7-day treatment and reported as a % (average) of the control tumor wt. (average) using 40 control rats. The results are summarized in Table 2.

TABLE 2

| Rats Survived/Tested | Dose (mg/kg) Per Injection | Tumor Evaluation (wt. mg) | Tumor wt % of Controls |
|---|---|---|---|
| 10/10 | 32.00 | 1557 | 68 |
| 10/10 | 16.00 | 2259 | 99 |
| 10/10 | 8.00 | 1817 | 80 |
| 39/40 | CNTRL | 2261 | |

At a dose of 32 mg/kg there was a 30% reduction in tumor growth. For such a short interval test (7 days) it appears there is an optimal dosage of about 30-40 mg/kg. It is expected that, over longer term tests, significant growth reduction would become more evident at the lower dosages as well. At higher doses (above 60 mg/kg) the results became poorer in this test.

We claim:
1. A pharmaceutical composition comprising
   (a) about 1 to about 10 parts of a compound of the formula:

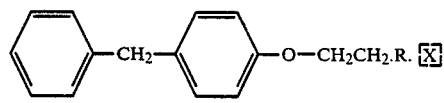

where R is

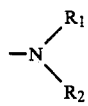

wherein $R_1$ and $R_2$ are ethyl groups and X when present, is a physiologically-acceptable salt forming acid; and, (b) about 1 part of 1-(p-β-dimethylaminoethoxyphenyl)-trans-1,2-diphenyl-but-1-ene or a physiologically acceptable salt thereof.

2. The composition of claim 1 wherein the compound (a) has X present as hydrochloric acid.

3. A method of treatment of human estrogen-stimulated breast cancer comprising administering to said human the composition of claim 1 within the dose range effective to inhibit the breast cancer cell growth.

4. A method of treatment of breast or colon cancer in humans comprising administering to said human, by at least one oral and parenteral route, the compound of the formula:

 (1)

wherein R is

wherein $R_1$ and $R_2$ are ethyl groups within the dose range effective to inhibit breast or colon cancer cell growth.

5. A method of treatment of breast or color cancer in humans comprising administering to said human a compound of the formula

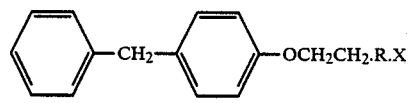 (2)

wherein R is as defined in claim 4 and X is a physiologically acceptable salt forming acid within the dose range effective to inhibit breast or colon cancer cell growth.

* * * * *